United States Patent [19]

Haerten

[11] 4,398,422
[45] Aug. 16, 1983

[54] ULTRASONIC-IMAGE DEVICE

[75] Inventor: Rainer Haerten, Roettenbach, Fed. Rep. of Germany

[73] Assignee: Siemens Aktiengesellschaft, Berlin & Munich, Fed. Rep. of Germany

[21] Appl. No.: 242,714

[22] Filed: Mar. 11, 1981

[30] Foreign Application Priority Data

Mar. 28, 1980 [DE] Fed. Rep. of Germany ....... 3012173

[51] Int. Cl.³ .......................................... G01N 29/04
[52] U.S. Cl. ...................................... 73/626; 128/660
[58] Field of Search ................. 73/626, 618, 625, 633, 73/634; 128/660

[56] References Cited

U.S. PATENT DOCUMENTS

| | | |
|---|---|---|
| 3,996,792 | 12/1976 | Kubota . |
| 4,103,677 | 8/1978 | Lansiart et al. ...................... 73/625 |
| 4,105,018 | 8/1978 | Greenleaf . |
| 4,120,291 | 10/1978 | Paton . |
| 4,174,705 | 11/1979 | Buchner ............................ 128/660 |
| 4,186,747 | 2/1980 | Iinuma . |
| 4,218,768 | 8/1980 | Hassler ................................ 73/612 |
| 4,235,111 | 11/1980 | Hassler ................................ 73/626 |
| 4,252,125 | 2/1981 | Iinuma et al. . |
| 4,341,120 | 7/1982 | Anderson ............................ 73/618 |

FOREIGN PATENT DOCUMENTS

| | | |
|---|---|---|
| 481693 | 9/1974 | Australia . |
| 2826828 | 7/1979 | Fed. Rep. of Germany . |
| 2425837 | 12/1979 | France . |
| 2015732 | 9/1979 | United Kingdom . |

OTHER PUBLICATIONS

Ito et al, "A New Real-Time Ultrasonic Diagnostic System for Dynamic and Still Images", *JEE*, Dec. 1978, pp. 60-64.

*Primary Examiner*—Anthony V. Ciarlante
*Attorney, Agent, or Firm*—Hill, Van Santen, Steadman & Simpson

[57] ABSTRACT

In an exemplary embodiment, an ultrasonic applicator for line-by-line ultrasonic scanning supplies echo signals to a device for displaying a layer image. The aim of the disclosure is to produce an imaging system which does not cause any coupling problems in any position of the application location; in addition, application should also be possible, in particular, in the chest area for obtaining subcostal sectional images. This aim is achieved by a line-by-line scanning applicator being also additionally pivotally or rotatably mounted, for the purpose of oscillation or rotation of the scanning surface, about such an oscillating-or rotating-axis, e.g. over a specifiable angular range and by a motor drive, with the applicator being firmly assigned to the selected application location during the angular movement.

17 Claims, 3 Drawing Figures

ULTRASONIC-IMAGE DEVICE

BACKGROUND OF THE INVENTION

The invention relates to an ultrasonic imaging apparatus with an ultrasonic applicator for line-by-line ultrasonic scanning and with a device for displaying an echo perspective representation.

An ultrasonic imaging apparatus of this type is known e.g. from the publication "A New Real-Time Ultrasonic Diagnostic System for Dynamic and Still Images" by K. Ito et al from the Medical Electronics Journal, JEE, December 78, pages 60 to 64. The ultrasonic applicator of this apparatus is specifically an ultrasonic array which already scans an area of examination line-by-line by means of electronic continuous beam switching operation. According to FIG. 2 of the publication, this ultrasonic array can be shifted parallel to itself by a motor drive along the surface of the examination subject. With a pure B-mode there are thus obtained sectional images of the examination subject that are parallel to one another and in time sequence. When using suitable time gates, scanning in the C-mode or in the F-mode is also possible. In the C-mode, plane sections are obtained which run perpendicularly to the beam direction at a specific depth of the examination subject. With a corresponding programming of the time delay of the time member, the F-mode delivers surfaces of any shape.

The special type of displacement of the ultrasonic array over a large surface brings problems with regard to the correct coupling between the array and the body surface. Besides, the application is limited to soft tissue, e.g. the stomach region. Subcostal layer images cannot be obtained because of the shadow effects of the ribs.

SUMMARY OF THE INVENTION

It is the object of the invention to provide an ultrasonic imaging apparatus of the type mentioned at the beginning, which does not cause any problems of coupling in any position at all of the region of application; in addition, application particularly in the chest region, for obtaining subcostal sectional images, e.g. of the heart or also the liver should also be possible.

The object is achieved according to the invention in that an applicator already scanning in line-by-line fashion, for the purpose of pivotally oscillating or rotating the scanning surface, is also additionally pivotally or rotatably support-mounted for movement about a pivot or rotational axis in a specifiable angular range, e.g. by means of a programmable motor drive, which, on application, is firmly assigned to the respective application location.

The invention allows large-surface scanning by pivoting oscillation and/or rotation of a scanning plane, with the axis of angular movement at a small stationary coupling surface; thus the coupling is simple and causes no problems. Application in the chest region for obtaining subcostal layer images is possible at any time because of the small coupling surface which guarantees a problem-free application or placement for penetration between or under the ribs. The application is not restricted to the obtaining of images in the B-mode; by addition of a suitable time gate circuit, switching can be effected, as with the image device of the article from Medical Electronics, for operation in the C-mode or F-mode, but without the disadvantages of this device. Likewise, when required, a transfer to two-dimensional Doppler-image representation is also possible.

Further advantages and details of the invention can be seen from the following description of two embodiments on the basis of the figures on the accompanying drawing sheet in conjunction with the subclaims; and other objects, features and advantages will be apparent from this detailed disclosure and from the appended claims.

DETAILED DESCRIPTION

Figure 1:
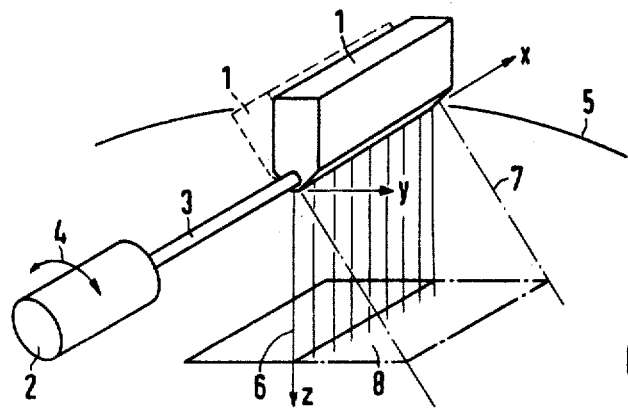
FIG. 1 shows a first embodiment with a pivotally oscillating ultrasonic array as an ultrasonic applicator.

In FIG. 1 an ultrasonic array for line-by-line ultrasonic scanning is designated by reference numeral 1. The ultrasonic array is pivotally support-mounted by motor drive 2 for oscillation about an axis of rotation 3 in the direction of the pivot arrow 4. The axis of rotation of a shaft 3 extends in the longitudinal direction of the application surface of the array 1. The pivotal support lies at a lateral surface near the application surface of the array. When contact is made on the surface of an object of examination, e.g. between the ribs of a patient to be examined, due to the pivotal oscillating movement of the ultrasonic-array 1, similarly to a sector scanner for an individual beam, pivoting or an oscillatory sweep of the scanning plane is possible. In FIG. 1, for example, the center scanning plane is indicated by 6 in the midposition of the applicator, while for a left oblique position of the array which is shown by dash lines in FIG. 1, there results the pivoted scanning plane indicated by dot-dash lines at 7. When transferring to C- or F-mode there is obtained, for example, when using suitable time gate circuits, the sectional plane indicated at 8.

Figure 2:
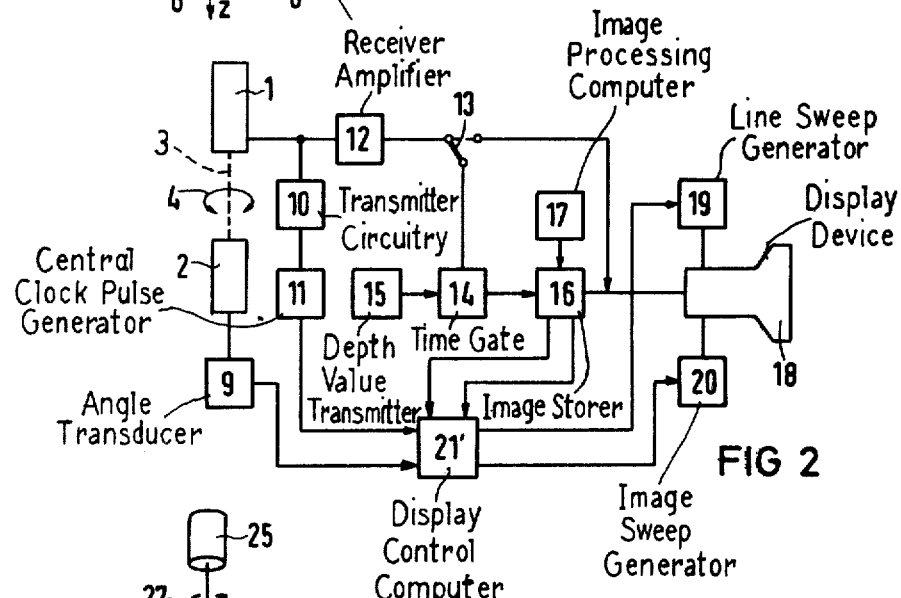
FIG. 2 shows the basic circuit diagram of an imaging system which uses such a pivotally oscillating ultrasonic array as applicator.

The basic circuit diagram of the image device which, e.g. works in conjunction with an ultrasonic array according to FIG. 1, is shown in FIG. 2. Here there is associated with the oscillatory drive motor 2 an angle transmitter 9, which, for each oscillatory movement, supplies the angular position signals necessary for the image composition. The transmitter circuitry for producing transmitting pulses is designated 10. It is controlled by a central clock pulse generator 11. The echo signals received are accepted by a receiver amplifier 12 and are delivered via a selector switch 13 either directly (for real time representation) or, via an intermediate processing circuit 14, 15, 16, 17, to an electron beam tube 18, with line sweep generator 19 and image sweep generator 20 as well as address computer 21', for controlling the display of the echo sectional image. Direct conveying (or, if necessary, also conveying via an intermediate store) leads to the representation in the B-mode. Representation in the C-mode or also in the F-mode is possible in the switch position of the selector switch 13 shown by the solid line in FIG. 2. In this switch position, echo signals of the amplifier 12 are supplied to a time gate 14 which, controlled by depth value transmitter 15, only transmits echo signals from a specifiable depth of the object under examination. The depth-selected echo signals allowed through in this manner are stored in an image storer 16 with associated computer 17 for image processing, in particular, single- or multidimensional spatial frequency-dependent filtering, and from there are called up for display on the viewing screen of the image tube 18. The depth value transmitter 15 is preferably a program transmitter which transmits constant depth values or depth values which are variable according to any desired functions. The computer 17 guarantees that, in the case of operation in the C-mode or also F-mode, uniform resolution over the entire surface area is provided.

Figure 3:
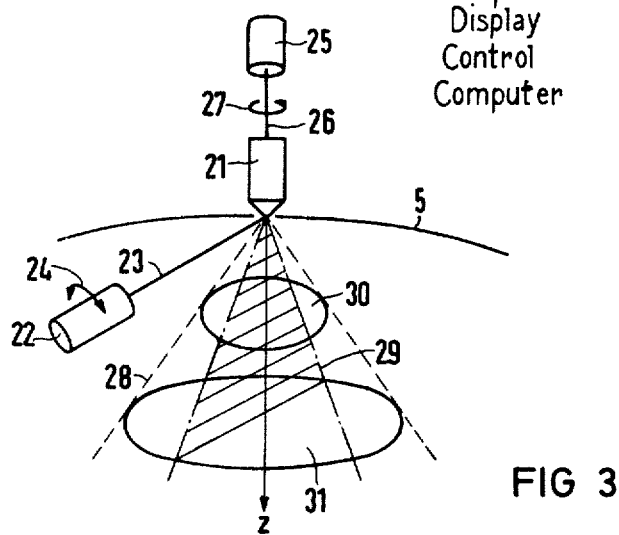
FIG. 3 shows an embodiment comprising a sector scanning head which is rotated about the Z axis and pivotally oscillated about an axis perpendicular to the Z axis.

FIG. 3 shows an embodiment with a sector scanning head 21. This sector scanning head is mechanically oscillated in the conventional way by an oscillatory drive motor 22 about a pivot axis 23 in the direction of the double arrow 24. A rotational movement of the scanning head 21 about the central axis of rotation 26 in the direction of arrow 27 is now additionally superimposed on the oscillatory movement in the specifiable angular range by means of rotary drive motor 25. The scanning sector is thus rotated and there results the scanning cone 28 shown in FIG. 3. Representation can again take place in the B-mode, i.e. an image is formed on the screen of the oscilloscope tube of the respective sector 29, rotated in steps. Likewise, by switching-over to C-mode, sectional planes of the type of the planes 30 and 31 can be obtained, or by switching to F-mode, differently shaped surfaces, e.g. curved, or the like, can also be obtained. The basic circuit diagram for an ultrasonic imaging device, which operates with an applicator according to FIG. 3, corresponds in the essential features to that of FIG. 2. In addition to the angle signals of the sector movement, only the angle signals of the rotational movement must also be detected and taken into account in the image representation.

It will be apparent that many modifications and variations may be effected without departing from the scope of the novel concepts and teachings of the present invention.

SUPPLEMENTARY DISCUSSION

FIG. 1 shows an ultrasonic array transducer 1 which may have a series of eighty or more ultrasonic transducer elements arranged along the longitudinal axis, designated as the x-axis in FIG. 1. The sequential excitation of individual ones of such transducer elements in a linear array, or the excitation of successively offset groups of such transducer elements, to shift an ultrasonic beam along the longitudinal axis is explained in detail, for example in U.S. Pat. Nos. 4,235,111 and 4,218,768, the disclosure of these patents being incorporated herein by reference.

The separation of the centers of the successive transducer elements may correspond to the longitudinal separation $\Delta x$ of successive image points of a layer. For scanning of the layer within plane 8 in FIG. 1, then, the resolution along the x-axis would correspond to such transducer element separation $\Delta x$. By way of example, the oscillatory motor 2 may be programmed to shift the transducer array 1 through an angle after each longitudinal scan of a scanning plane (such as 6 or 7, FIG. 1) such that the separation between the longitudinal scan lines in the layer plane 8, which separation may be designated $\Delta y$, will be equal to the value $\Delta x$ over the entire body layer of interest. Thus the image points resolved in the plane 8 may be equally spaced with respect to directions parallel to the x and y axes in FIG. 1. The programmed stepping of motor 2 in this manner is clearly within the skill of the art. For example a stepping motor (which is reversible) can be selected such that its minimum step interval of angular displacement is small compared to the minimum step angle of shaft 3 which may be required. Then ordinary numerical control techniques may be utilized to effect the necessary varying angular stepping of applicator 1 between successive longitudinal scans of the array 1.

For the scanning of a body layer in plane 8, FIG. 1, the time gate circuit 14 would, of course, be programmed to transmit echoes from this layer for each angular position of array 1. Thus as the array was pivoted from the perpendicular position shown in solid outline in FIG. 1 to the extreme oblique position indicated by dash lines, the time gate circuit 14 would increase the time lag after a transmission pulse at which the time gate would be placed in the transmitting condition for echo signals from receiving amplifier 12. Such a varying time lag can be controlled by a digital countdown counter which is loaded with successive preprogrammed time lag counts which are then counted to zero by a standard clock pulse rate signal to effect momentary transmission of echo signals by the time gate circuit 14.

Any scanning operation in B-mode, C-mode and/or F-mode may be recorded in analog form for subsequent processing and display, or converted to digital form and stored in a digital memory for later processing.

For the example of FIG. 3, with a step increment of rotation of the ultrasonic transducer 21 about the z-axis alternating with each oscillatory scan cycle, the resolution in the direction arcuately about the z-axis would vary with the distance from the z-axis; however at each radial distance from the z-axis the resolution in the radial direction (e.g. determined by the rate of supply of transmit pulses to transducer 21) could correspond to the resolution in the arcuate direction at such radius.

An example of an electronic sector scanner applicable to the arrangement of FIG. 3 is found in U.S. Pat. No. 4,163,394, such scanner being susceptible to stepwise rotation about an axis perpendicular to the application region of a body 5 as represented by the z-axis in FIG. 3 of the present drawings. For example, the arcuate sector array (3, 4) of U.S. Pat. No. 4,163,394 could be rotated step by step about a central z-axis with the window (6) stationary and engaged against the body surface firmly. A similar type of support mounting could be used for the array 1, FIG. 1, and for transducer head 21, FIG. 3, so that there would be a stationary window membrane interposed between the application surface of array 1 or head 21 and the body surface 5.

It will be understood by those skilled in the art that the rounded application surface of applicator 1, FIG. 1, can be directly and firmly engaged with a desired body surface such as indicated at 5, the curvature of the application surface being essentially a circular arc so that axis 3 readily remains at a fixed spacing from the layer under examination, such as 8, during a scanning operation.

In FIG. 3, motor 25 may be driven in an oscillatory manner, instead of being unidirectionally driven.

The computer 17 associated with the image storer 16 may process C-mode and F-mode images especially to provide one-dimensional or multi-dimensional spacial frequency dependent filtering.

A Doppler device for detecting Doppler signals from moving parts of an examination subject may be selectively coupled with ultrasonic applicator 1 or 21 for the sensing of two-dimensional ultrasonic Doppler images of such moving parts of the examination subject.

I claim as my invention:

1. An ultrasonic imaging system comprising an ultrasonic applicator for ultrasonic scanning of a layer of an examination object, and a display device for providing an echo image display,
   (a) first scanning means for operating said applicator to effect scanning in a line-by-line fashion with an ultrasonic beam directed generally in a depth direction so as to sweep a scanning plane (6, 7; 29), and
   (b) second scanning means mounting said applicator for angular movement about an axis (3; 26) so as to successively offset the scanning plane angularly and to sweep a scanning volume within an examination object, said second scanning means comprising a mechanical drive (2; 25) coupled with said applicator for effecting the angular movement thereof about said axis,
   (c) said ultrasonic applicator comprising a longitudinally extended ultrasonic array (1), said first scanning means (10) serving to operate said ultrasonic array (1) by sequential electronic beam switching so as to offset the ultrasonic beam in a longitudinal direction in sweeping the scanning plane (6, 7), and said second scanning means mounting said ultrasonic array (1) for oscillatory movement about a pivot axis (3) which extends in the longitudinal direction of said ultrasonic array (1),
   (d) said mechanical drive comprising an oscillatory drive motor (2) for effecting the oscillatory movement of the ultrasonic array (1) about said pivot axis (3), through successive angular positions, said pivot axis (3) remaining at a fixed spacing relative to the examination object at a given application location,
   (e) operating means coupled with said ultrasonic applicator for operating the ultrasonic applicator for scanning over a layer conforming with a surface different from said scanning plane and extending through the scanning volume, and an image storer (16) for storing echo signals, said operating means including a time gate circuit (14, 15), and means operable in one mode to supply the echo signals to the image storer (16) under the control of the time gate circuit (14, 15).

2. An ultrasonic imaging system according to claim 1, with said ultrasonic array (1) having a longitudinally extended application surface which is rounded relative to the pivot axis (3) so as to accommodate maintenance of said fixed spacing of the pivot axis (3) relative to said examination object during pivotal oscillation of said ultrasonic array about said pivot axis, said ultrasonic array having at least one lateral surface near said rounded application surface and said oscillatory drive motor (2) being coupled with said ultrasonic array at said lateral surface.

3. An ultrasonic imaging apparatus according to claim 1, with said operating means being coupled with said ultrasonic applicator for selectively operating the ultrasonic applicator for B-mode scanning over a layer lying in the scanning plane, for C-mode scanning over a layer conforming with a plane lying generally transverse to said scanning plane and within the scanning volume, and for F-mode scanning over a layer conforming with an arbitrary surface extending through the scanning volume.

4. An ultrasonic imaging system according to claim 3, said operating means being operable in another mode to supply echo signals from the ultrasonic applicator directly to the display device (18).

5. An ultrasonic imaging system according to claim 4, with a computer (17) associated with the image storer (16) for processing C-mode and F-mode images.

6. An ultrasonic imaging system according to claim 1, with said mechanical drive (2; 25) being operable for C-mode and F-mode scanning over said layer and providing angular movement about said axis (3; 26) in steps so programmed that for each point of a selected layer there results a substantially equidistant arrangement of image points on said layer.

7. An ultrasonic imaging system according to claim 1, said ultrasonic array (1) having a longitudinally extended application surface which is rounded relative to the pivot axis (3) so as to accommodate maintenance of said fixed spacing of the pivot axis (3) relative to said layer of the examination object during pivotal oscillation of said ultrasonic array about said pivot axis.

8. An ultrasonic imaging system according to claim 1, with said ultrasonic array (1) having a longitudinally extended application surface, and said pivot axis (3) being near said application surface so as to minimize the angular movement of the application surface of said ultrasonic array relative to an application location during a scanning operation.

9. An ultrasonic imaging apparatus according to claim 1, with said operating means being operable for scanning over a layer conforming with a plane lying generally transverse to said scanning plane and within the scanning volume.

10. An ultrasonic imaging system according to claim 9, with said computer (17) being operable for processing layer images to effect spatial frequency dependent filtering thereof.

11. An ultrasonic imaging system comprising an ultrasonic applicator for ultrasonic scanning of a layer of an examination object, and a display device for providing an echo image display,
   (a) first scanning means for operating said applicator to effect scanning in a line-by-line fashion with an ultrasonic beam directed generally in a depth direction so as to sweep a scanning plane (6, 7; 29), and
   (b) second scanning means mounting said applicator for angular movement about an axis (3; 26) so as to successively offset the scanning plane angularly and to sweep a scanning volume within an examination object, said second scanning means comprising a mechanical drive (2; 25) coupled with said applicator for effecting the angular movement thereof about said axis,
   (c) said first scanning means operating said applicator (21) to effect line-by-line sector scanning so as to sweep a sector (29) in a scanning plane, said second scanning means mounting said ultrasonic applicator for angular movement about an axis (26) which is generally in a depth direction,
   (d) said mechanical drive comprising a motor (25) for effecting angular movement of said applicator about said axis (26) through successive angular positions, said axis (26) thereby remaining in a fixed position relative to the examination object at a given application location,
   (e) operating means coupled with said ultrasonic applicator for operating the ultrasonic applicator for scanning over a layer conforming with a surface different from said scanning plane and extending through the scanning volume, and an image storer (16) for storing echo signals, said operating means including a time gate circuit (14, 15), and means operable in one mode to supply the echo signals to the image storer (16) under the control of the time gate circuit (14, 15).

12. An ultrasonic imaging apparatus according to claim 11, wherein said operating means are coupled with said ultrasonic applicator for selectively operating the ultrasonic applicator for B-mode scanning over a layer lying in the scanning plane, for C-mode scanning over a layer conforming with a plane lying generally transverse to said scanning plane and within the scanning volume, and for F-mode scanning over a layer conforming with an arbitrary surface extending through the scanning volume.

13. An ultrasonic imaging system according to claim 12, wherein said operating means are operable in another mode to supply echo signals from the ultrasonic applicator directly to the display device (18).

14. An ultrasonic imaging system according to claim 13, with a computer (17) associated with the image storer (16) for processing C-mode and F-mode images.

15. An ultrasonic imaging system according to claim 14, wherein said computer (17) is provided for processing layer images to effect spatial frequency dependent filtering thereof.

16. An ultrasonic imaging system according to claim 11, with said mechanical drive (25) being operable for C-mode and F-mode scanning over said layer and providing angular movement about said axis (26) in steps so programmed that for each point of a selected layer there results a substantially equidistant arrangement of image points on said layer.

17. An ultrasonic imaging apparatus according to claim 11, wherein said operating means are provided for scanning over a layer conforming with a plane lying generally transverse to said scanning plane and within the scanning volume.

* * * * *